United States Patent
Yamamoto et al.

(10) Patent No.: US 7,138,484 B2
(45) Date of Patent: Nov. 21, 2006

(54) METHOD FOR PRODUCING POLYMERIZED HYDROCARBON

(75) Inventors: Takakazu Yamamoto, Yokohama (JP); Naoyuki Kitamura, Tokyo (JP); Hiroki Fukumoto, Yokohama (JP)

(73) Assignee: JFE Chemical Corporation, Tokyo (JP)

( * ) Notice: Subject to any disclaimer, the term of this patent is extended or adjusted under 35 U.S.C. 154(b) by 0 days.

(21) Appl. No.: 10/952,731

(22) Filed: Sep. 30, 2004

(65) Prior Publication Data

US 2005/0075478 A1    Apr. 7, 2005

(30) Foreign Application Priority Data

Sep. 30, 2003    (JP)    ............................. 2003-340301

(51) Int. Cl.
   *C08G 61/00*    (2006.01)
(52) U.S. Cl. ...................... 528/394; 528/488; 528/373
(58) Field of Classification Search ................ 528/397, 528/488, 373
   See application file for complete search history.

(56) References Cited

U.S. PATENT DOCUMENTS

| | | |
|---|---|---|
| 4,554,104 A | 11/1985 | Kapur et al. |
| 5,396,006 A | 3/1995 | Wettling et al. |
| 6,552,237 B1 | 4/2003 | Bedbury et al. |

FOREIGN PATENT DOCUMENTS

| | | |
|---|---|---|
| JP | 63132906 | 4/1988 |
| JP | 2015063 | 1/1990 |

*Primary Examiner*—Duc Truong
(74) *Attorney, Agent, or Firm*—Young & Thompson

(57) ABSTRACT

A method for producing a polymerized hydrocarbon includes a step of a dehalogenation of a halogenated hydrocarbon with a magnesium-diene complex. Low-molecular-weight compounds, such as dimers or trimers of hydrocarbon units, oligomers of hydrocarbon units, or polymers of hydrocarbon units can be produced by this method while generating significantly less odor.

7 Claims, No Drawings

METHOD FOR PRODUCING POLYMERIZED HYDROCARBON

BACKGROUND OF THE INVENTION

1. Field of the Invention

The present invention related to a method for producing a polymerized hydrocarbon by dehalogenation of a halogenated hydrocarbon. In this method, a new carbon-carbon bond (C—C bond) is formed by the dehalogenation of the halogenated hydrocarbon, and a polymerized hydrocarbon containing two or more molecules of hydrocarbon unit by condensation can be produced.

2. Description of the Related Art

Methods for producing polymerized hydrocarbons by dehalogenation of halogenated hydrocarbons using zerovalent nickel complexes have been known in the art. Among these methods, the Yamamoto method that uses biscyclooctadienyl nickel(0) is highly versatile since it can be used to synthesize not only low-molecular-weight compounds, such as dimers and trimers of hydrocarbons, but also oligomers and polymers of hydrocarbons (T. Yamamoto, T. Ito, K. Kubota, Chem. Lett., 153 (1988); and T. Yamamoto, A. Morita, Y. Miyazaki, T. Maruyama, H. Wakayama, Z.-H. Zhou, Y. Nakamura, T. Kanbara, S. Sasaki, and K. Kubota, Macromolecules 25, 1214 (1992)). However, the method using biscyclooctadienyl nickel(0) produces cyclooctadiene with a pungent odor as a byproduct. Because of this odor, the reaction handling and the treatment following the reaction become difficult, thereby requiring a complicated facility for processing. A method for producing polymerized hydrocarbon while repressing the pungent odor is desired.

SUMMARY OF THE INVENTION

Accordingly, it is an object of the present invention to provide a method for producing polymerized hydrocarbon whereby the odor is repressed.

To achieve this object, the present invention provides a method for producing a polymerized hydrocarbon, including a step of a dehalogenation of a halogenated hydrocarbon with a magnesium-diene complex.

Preferably, the halogenated hydrocarbon is represented by General Formula (1) or (3), and the polymerized hydrocarbon is represented by General Formula (2) or (4):

$$2X-R + Mg(Diene) \rightarrow \quad (1)$$

$$R-R + MgX_2 + Diene \quad (2)$$

$$nX'-R-X'' + nMg(Diene) \rightarrow \quad (3)$$

$$-(R)_n + nMgX'X'' + n\, Diene \quad (4)$$

(wherein each R represents a hydrocarbon group that may contain a heteroatom; X, X', and X" each represent a halogen atom; and n represents an integer of 2 or more).

Preferably, a diene as a raw material for constituting the magnesium-diene complex is a conjugated diene.

More preferably, the magnesium-diene complex is (2-butene-1,4-diyl)magnesium.

Preferably, the dehalogenation is performed in the presence of a nickel complex catalyst or a palladium complex catalyst.

Preferably, Rs in general formulae (1) to (4) have conjugated multiple bonds.

Preferably, Rs in general formulae (1) to (4) each contain at least one ring structure selected from the group consisting of rings of benzene, thiophene, fluorene, and pyridine. More preferably, the ring structure further has a substituent.

The present invention also provides a method for producing a hydrocarbon containing a carbon-carbon bond, the method including a step of dehalogenating a halogenated hydrocarbon, in which a magnesium-diene complex is used as a dehalogenating agent.

DESCRIPTION OF THE PREFERRED EMBODIMENTS

The present invention will now be described by preferred embodiments.

In the present invention, a polymerized hydrocarbon is produced by reacting a halogenated hydrocarbon with a magnesium-diene complex, thereby producing a new C—C bond by dehalogenation of a halogenated hydrocarbon. In other words, the present reaction is a condensation of the halogenated hydrocarbon by the removal of the halogen. The resulting product, a polymerized hydrocarbon, of the present invention is a condensation product of two or more hydrocarbon molecules of the halogenated hydrocarbon, e.g., a low-molecular-weight hydrocarbon compound such as dimer or trimer, or a high-molecular-weight hydrocarbon compound such as an oligomer or a polymer.

Preferably, the halogenated hydrocarbon represented by general formula (1) or (3) described above is dehalogenated by a reaction with a magnesium-diene complex to produce the polymerized hydrocarbon represented by general formula (2) or (4) described above.

For example, a compound represented by general formula (2) can be produced at high reaction efficiency when 1 mol of a halogenated hydrocarbon represented by general formula (1) is reacted with 0.5 to 2 mol of a magnesium-diene complex in a solution to conduct dehalogenation. A compound represented by general formula (4) can be produced at high reaction efficiency when 1 mol of a halogenated hydrocarbon represented by general formula (3) is reacted with 1 to 3 mol of a magnesium-diene complex in a solution to conduct dehalogenation. The dehalogenation reaction is preferably performed in the presence of 0.1 mmol to 10 mol and, more preferably, 0.01 to 0.5 mol of a catalyst per mole of halogenated hydrocarbon to increase the reaction efficiency.

In the present invention a hydrocarbon group represented by R refers to an organic group containing hydrogen and carbon, e.g., an aliphatic group, an aromatic group, an alicyclic group, or a heterocyclic group. The hydrocarbon group may contain a heteroatom such as a sulfur atom, a nitrogen atom, a phosphorus atom, an oxygen atom, or a silicon atom. The hydrocarbon group preferably contains 1 to 60 carbon atoms since such a hydrocarbon group is soluble in a solvent described below and is thus suitable for dehalogenation.

The compound represented by general formula (1) is a monohalide, i.e., a hydrocarbon, such as an aromatic or aliphatic compound, having an atom replaced with a halogen atom. Preferable examples thereof include 2-bromo-9,9-diarylfluorene, 2-iodo-9,9-diarylfluorene, 2-bromo-9,9-dialkylfluorene, 2-iodo-9,9-dialkylfluorene, 2-bromothiophene, 2-iodothiophene, 2-bromo-3-hexylthiophene, 2-iodo-3-methylthiophene, bromobithiophene, iodobithiophene, bromoterthiophene, iodoterthiophene, bromobipyridine, iodobipyridine, bromoterpyridine, iodoterpyridine, bromopyridine, iodopyridine, bromobenzene, 1-bromo-2,5-dialkoxybenzene, iodobenzene, bromobenzothiadiazole, iodobenzothiadiazole, bromocarbazole, iodocarbazole, bromonaphthalene, iodonaphthalene, bromoanthracene, iodoanthracene, bromoquinoline, iodoquinoline, bromobiphenyl, iodobiphenyl, bromoterphenyl, iodoterphenyl, bromophenanthroline, and iodophenanthroline.

The compound represented by general formula (3) is a dihalide, i.e., a hydrocarbon, such as an aromatic or aliphatic compound, having two atoms replaced with two halogen atoms. The halogen atoms represented by X' and X" may be the same or different. Preferable examples of the dihalide include 2,7-dibromo-9,9-diarylfluorene, 2,7-diiodo-9,9-diarylfluorene, 2,7-dibromo-9,9-dialkylfluotene, 2,7-diiodo-9,9-dialkylfluorene, 2,5-dibromothiophene, 2,5-diiodothiophene, 2,5-dibromo-3-hexylthiophene, 2,5-diiodo-3-methylthiophene, dibromobithiophene, diiodobithiophene, dibromoterthiophene, diiodoterthiophene, dibromobipyridine, diiodobipyridine, dibromoterpyridine, diiodoterpyridine, dibromopyridine, diiodopyridine, 1,4-dibromobenzene, 1,4-dibromo-2,5-dialkoxybenzene, 1,4-diiodobenzene, dibromobenzothiadiazole, diiodobenzothiadiazole, dibromocarbazole, diiodocarbazole, dibromonaphthalene, diiodonaphthalene, dibromoanthracene, diiodoanthracene, dibromoquinoline, diiodoquinoline, dibromobiphenyl, diiodobiphenyl, dibromoterphenyl, diiodoterphenyl, dibromophenanthroline, and diiodophenanthroline.

These monohalides or dihalides may be used alone or in combination. The halogen in the halogenated hydrocarbon is preferably bromine. The halogenated hydrocarbon can be selected according to the application of the resulting products. For example, when the resulting product is to be used as a high-quality luminescent material, hydrocarbons having conjugated multiple bonds are preferred. Preferable examples of such hydrocarbons include those having benzene, thiophene, fluorene, or pyridine rings which may have a substituent.

The magnesium-diene complex used in the present invention is synthesized by the reaction between metallic magnesium and a diene compound. Examples of the magnesium-diene complex include (2-butene-1,4-diyl)magnesium: [MgCH$_2$CH=CHCH$_2$] (thf)$_2$, (2-methyl-2-butene-1,4-diyl) magnesium: [MgCH$_2$C(CH$_3$)=CHCH$_2$] (thf)$_2$, (2,3-dimethyl-2-butene-1,4-diyl)magnesium: [MgCH$_2$C(CH$_3$)=C(CH$_3$)CH$_2$] (thf)$_2$, and (1,4-diphenyl-2-butene-1,4-diyl)magnesium: [MgCH(C$_6$H$_5$)CH=CHCH(C$_6$H$_5$)] (thf)$_3$. Here, "thf" represents tetrahydrofuran. (2-Butene-1,4-diyl)magnesium, which provides high dehalogenation efficiency and is widely available, is particularly preferred.

In the present invention, the halogenated hydrocarbon is preferably reacted with the magnesium-diene complex in the presence of a catalyst. Preferable examples of the catalyst include palladium(II) complexes such as Pd(dppb)Cl$_2$, nickel(II) complexes such as Ni(dppp)Cl$_2$, palladium(0) complexes, nickel(0) complexes, cobalt complexes such as cobalt chloride, iron(II) complexes such as iron chloride, and iron(III) complexes. Here, "dppb" denotes diphenylphosphinobutane, and "dppp" denotes diphenylphosphinopropane. In particular, a nickel or palladium complex is preferred as the catalyst for increasing the dehalogenation efficiency.

The reaction is preferably performed in an organic solvent. A common solvent, such as tetrahydrofuran, dialkyl ether, toluene, or xylene, may be used as the solvent. The solvent is preferably dried in advance over anhydrous sodium sulfate, metallic alkali and/or a hydride compound. The reaction temperature depends on the amount of the feed, the amount of the solvent, and the type of solvent. The temperature is preferably sufficiently high to prevent solidification of the reaction mixture, which results in inhibition of the reaction. The temperature is preferably sufficiently low to prevent evaporation of the solvent, the materials, and the like in large amounts. In general, the reaction temperature is in the range of 10° C. to the reflux temperature of the solvent, and preferably in the range of 40° C. to 100° C. The reaction time is preferably 1 to 72 hours.

The resulting reaction mixture is washed with an appropriate washing solvent for an appropriate number of times to isolate the polymerized hydrocarbon from the solvent, the magnesium-diene complex, the halogenated hydrocarbon, magnesium halide, and diene.

The above-described method for producing a polymerized hydrocarbon from a halogenated hydrocarbon by using a magnesium-diene complex can be applied to synthesis of various organic compounds, oligomers, and polymers. Compared to conventional methods that use biscyclooctadienyl nickel, odor can be suppressed.

EXAMPLES

The present invention will now be described by way of nonlimiting examples.

Example 1

Synthesis of poly(9,9-dioctylfluorene-2,7-diyl) (1)

In a 50 ml Schlenk tube purged with an inert gas, 0.520 g (0.948 mmol) of 2,7-dibromo-9,9-dioctylfluorene, 8.1 mg (0.015 mmol) of Ni(dppp)Cl$_2$, 20 ml of dry tetrahydrofuran, 2.4 ml (1.27 mmol) of a tetrahydrofuran suspension of (2-butene-1,4-diyl)magnesium were charged. The mixture was reacted for 35 hours at room temperature and 5 hours at a reflux temperature while stirring. The reaction solution was then fed into a mixture of methanol and concentrated hydrochloric acid (10:1) to terminate the polymerization. The supernatant was removed by decantation to recover the product. The product was subjected to a typical purification process such as acid washing and alkali washing. After drying, 0.507 g of a pale chrome yellow slurry was obtained. No odor was detected during the synthesis of EXAMPLE 1.

Table 1.1. shows the reaction conditions, the yield of the product, poly(9,9-dioctylfluorene-2,7-diyl), and the number-average molecular weight (Mn) and weight-average molecular weight (Mw) determined by gel permeation chromatography (GPC).

Example 2

Synthesis of poly(9,9-dioctylfluorene-2,7-diyl) (2)

In a 50 ml Schlenk tube purged with an inert gas, 0.615 g (1.12 mmol) of 2,7-dibromo-9,9-dioctylfluorene, 0.0339 g (0.0561 mmol) of Pd(dppb)Cl$_2$, and 15 ml of dry toluene were charged. After 1.5 hours of stirring at room temperature, 3.2 ml (1.7 mmol) of a tetrahydrofuran suspension of (2-butene-1,4-diyl)magnesium was added, and the resulting mixture was reacted for 35 hours at room temperature and 5 hours at the reflux temperature of the solvent (toluene/tetrahydrofuran) while stirring. The reaction solution was fed into a mixture of methanol and concentrated hydrochloric acid (7:1) to terminate the polymerization. The product was recovered by suction filtration, subjected to a typical purification process such as acid washing, alkali washing, and reprecipitation, and dried to obtain 0.358 g of a pale yellow, powdery polymer, poly(9,9-dioctylfluorene-2,7-diyl). The results of analysis of this powder are shown below. No odor was detected during the synthesis in EXAMPLE 2.

Results of elemental analysis:
Calculated value: C=89.63 percent by mass, H=10.37 percent by mass
Observed value: C=88.60 percent by mass, H=10.46 percent by mass (The calculated values are for poly(9,9-dioctylfluorene-2,7-diyl).)

Table 1.1. shows the reaction conditions, the yield of the product, poly(9,9-dioctylfluorene-2,7-diyl), and the number-average molecular weight (Mn) and weight-average molecular weight (Mw) determined by gel permeation chromatography (GPC).

Example 3

Synthesis of poly(9,9-dioctylfluorene-2,7-diyl) (3)

The compound is synthesized as in EXAMPLES 1 and 2 but with different reaction conditions. Table 1.2. shows the reaction conditions, the yield of the product, poly(9,9-dioctylfluorene-2,7-diyl), and the number-average molecular weight (Mn) and weight-average molecular weight (Mw) determined by gel permeation chromatography (GPC) of four samples of EXAMPLE 3. No odor was detected during the synthesis in EXAMPLE 3.

TABLE 1.1

| No. | | EXAMPLE 1 | EXAMPLE 2 |
|---|---|---|---|
| Yield (%) | | trace | 82 |
| Magnesium-diene complex/halogenated hydrocarbon (molar ratio) | | 1.3 | 1.5 |
| Type of catalyst | | Ni(dppp)Cl$_2$ | Pd(dppb)Cl$_2$ |
| Catalyst/halogenated hydrocarbon (molar ratio) | | 0.016 | 0.050 |
| Solvent | | THF | Toluene/THF |
| Reaction temperature and reaction time | | 35 h at room temperature, 5 h at boiling point of solvent | 35 h at room temperature, 5 h at boiling point of solvent |
| GPC*[3] | Mn*[1] | Undetectable | 2,400 |
| | Mw*[2] | Undetectable | 3,600 |

*[1] number-average molecular weight
*[2] weight-average molecular weight
*[3] gel permeation chromatography (polystyrene equivalent)

Example 4

Synthesis of poly(thiophene-2,5-diyl)

In a 50 ml Schlenk tube purged with an inert gas, 0.662 g (2.74 mmol) of 2,5-dibromothiophene, 0.0827 g (0.137 mmol) of Pd(dppb)Cl$_2$, and 19 ml of dry tetrahydrofuran were charged. After 0.8 hour of stirring at room temperature, 7.7 ml (4.1 mmol) of a tetrahydrofuran suspension of (2-butene-1,4-diyl)magnesium was added, and the resulting mixture was reacted for 37 hours at room temperature and 11 hours at a reflux temperature while stirring. The reaction solution was then fed into a mixture of methanol and concentrated hydrochloric acid (7:1) to terminate the polymerization. The product was recovered by suction filtration, subjected to a typical purification process such as acid washing, alkali washing, and reprecipitation, and dried to obtain 0.190 g of a dark brown powder. The powder was identified as containing poly(thiophene-2,5-diyl) by elemental analysis. No odor was detected during the synthesis in EXAMPLE 4.

Example 5

Synthesis of poly(3-hexylthiophene-2,5-diyl)

In a 50 ml Schlenk tube purged with an inert gas, 0.964 g (2.29 mmol) of 3-hexyl-2,5-diiodothiophene, 0.0583 g (0.0966 mmol) of Pd(dppb)Cl$_2$, and 15 ml of dry tetrahydrofuran were charged. After 1 hour of stirring at room temperature, 5.4 ml (2.9 mmol) of a tetrahydrofuran suspension of (2-butene-1,4-diyl)magnesium was added, and the resulting mixture was reacted at room temperature for 35 hours and at a reflux temperature for 5 hours while stirring. The reaction solution was then fed into a mixture of methanol and concentrated hydrochloric acid (7:1) to terminate the polymerization. The supernatant was removed by decantation to recover the product. The product was subjected to a typical polymer purification process such as acid washing and alkali washing. After drying, 0.221 g of a dark red slurry was obtained. The slurry was identified as containing poly

TABLE 1.2

| | | EXAMPLE 3 | | | |
|---|---|---|---|---|---|
| No. | | 1 | 2 | 3 | 4 |
| Yield (%) | | 29 | 83 | 80 | 71 |
| Magnesium-diene complex/halogenated hydrocarbon (molar ratio) | | 1.5 | 1.5 | 1.5 | 1.5 |
| Type of catalyst | | Ni(dppp)Cl$_2$ | Pd(dppb)Cl$_2$ | Pd(dppb)Cl$_2$ | Pd(dppb)Cl$_2$ |
| Catalyst/halogenated hydrocarbon (molar ratio) | | 0.19 | 0.10 | 0.051 | 0.020 |
| Solvent | | THF | THF | THF | THF |
| Reaction temperature and reaction time | | 35 h at room temperature, 5 h at boiling point of solvent | 35 h at room temperature, 5 h at boiling point of solvent | 35 h at room temperature, 5 h at boiling point of solvent | 35 h at room temperature, 5 h at boiling point of solvent |
| GPC*[3] | Mn*[1] | 1,600 | 1,700 | 2,500 | 2,000 |
| | Mw*[2] | 3,300 | 2,500 | 3,900 | 2,800 |

*[1] number-average molecular weight
*[2] weight-average molecular weight
*[3] gel permeation chromatography (polystyrene equivalent)

(3-hexylthiophene-2,5-diyl) by elemental analysis. No odor was detected during the synthesis in EXAMPLE 5.

Example 6

Synthesis of Biphenyl

In a 50 ml Schlenk tube purged with an inert gas, 0.357 g (2.27 mmol) of bromobenzene, 0.0347 g (0.0575 mmol) of Pd(dppb)Cl$_2$, and 15 ml of dry tetrahydrofuran were fed. After 1 hour of stirring at room temperature, 3.2 ml (1.7 mmol) of a tetrahydrofuran suspension of (2-butene-1,4-diyl)magnesium was added, and the resulting mixture was reacted at room temperature for 35 hours and at a reflux temperature for 5 hours while stirring. The reaction solution was then fed into diluted hydrochloric acid to terminate the polymerization. The reaction product was extracted with diethyl ether and dried to obtain a pale yellow powder. The powder was identified as containing biphenyl by gas chromatography. No odor was detected in EXAMPLE 6.

Comparative Example 1

Poly(9,9-dioctylfluorene-2,7-diyl) was synthesized by the Yamamoto method. A pungent odor was detected during the synthesis in COMPARATIVE EXAMPLE 1.

According to the method of the present invention, not only oligomers but also polymers can be produced using various halogenated low-molecular-weight compounds as the starting materials. Furthermore, the method produces a significantly less odor and is environmentally friendly compared to conventional methods that use biscyclooctadienyl nickel(0).

According to the method of the present invention, oligomerization or polymerization of dioctylfluorene or thiophene derivatives is possible. Synthesis of biphenyl from bromobenzene is also possible. The method can be applied to coupling, oligomerization, or polymerization of other halogenated hydrocarbons. The polymerized hydrocarbon produced by the present invention can be used as a highly versatile luminescent material.

What is claimed is:

1. A method for producing a polymerized hydrocarbon, comprising:
a dehalogenation of a halogenated hydrocarbon with a magnesium-diene complex wherein the halogenated hydrocarbon is represented by General Formula (1) or (3), and the polymerized hydrocarbon is represented by General Formula (2) or (4):

$$2X\text{-}R+Mg(Diene) \rightarrow \quad (1)$$

$$R\text{—}R+MgX_2+Diene \quad (2)$$

$$nX'\text{—}R\text{-}X''+nMg(Diene) \rightarrow \quad (3)$$

$$R_n+nMgX'X''+n\ Diene \quad (4)$$

(wherein each R represents a hydrocarbon group that may contain a heteroatom; X, X', and X" each represent a halogen atom; and n represents an integer of 2 or more).

2. The method according to claim 1, wherein a diene as a raw material for constituting the magnesium-diene complex is a conjugated diene.

3. The method according to claim 1, wherein the magnesium-diene complex is (2-butene-1,4-diyl)magnesium.

4. The method according to claim 1, wherein the dehalogenation is performed in the presence of a nickel complex catalyst or a palladium complex catalyst.

5. The method according to claim 1, wherein Rs in general formulae (1) to (4) have conjugated multiple bonds.

6. The method according to claim 1, wherein Rs in general formulae (1) to (4) each contain at least one ring structure selected from the group consisting of rings of benzene, thiophene, fluorene, and pyridine.

7. The method according to claim 6, wherein the ring structure further has a substituent.

* * * * *